United States Patent [19]

Barberet et al.

[11] Patent Number: Plant 6,368

[45] Date of Patent: Nov. 1, 1988

[54] CARNATION NAMED 'LONSATO'

[75] Inventors: Nicole Barberet; Yves Duclox, both of Antibes, France

[73] Assignee: Laboratoire de Physiologie Vegetale de la Londe, La Londe, France

[21] Appl. No.: 907,860

[22] Filed: Sep. 15, 1986

[30] Foreign Application Priority Data

Jun. 20, 1986 [ES] Spain ..... 861485

[51] Int. Cl.[4] ..... A01H 5/00

[52] U.S. Cl. ..... Plt./70

[58] Field of Search ..... Plt./70

*Primary Examiner*—James R. Feyrer

*Attorney, Agent, or Firm*—Charles W. Rummler

[57] ABSTRACT

An original variety of standard carnation having medium sized blooms of a fiery red coloration produced profusely at recurrent intervals of spring, midseason and fall, the flowers being carried on long, strong and erect stems having rather abundant foliage, and the plant itself being distinguished by its tall growth and its vigorous, upright and very rigid growth habit with few branches.

1 Drawing Sheet

BACKGROUND OF THE NEW PLANT

This carnation variety originated as a seedling at La Londe, Les Maures, France, resulting from the crossing of plants selected from our collection of carnations maintained for breeding purposes at La Londe, our objective in making this crossing being to develop new carnations having blooms of good quality and excellent color on strong plants having resistance to *Fusarium oxysporum.* This plant was selected from the seedlings resulting from the said crossing because of its very extraordinary flower coloration and its apparently vigorous and strong growth habit. Propagation of this selected plant was carried on under our direction at La Londe by cuttings and in vitro propagation through several successive generations, which clearly demonstrated that the novel characteristics of its blooming and growth habits appeared to be firmly fixed and would remain true from generation to generation.

DESCRIPTION OF THE DRAWING

This new variety of standard carnation is illustrated by the accompanying photographic drawing which shows, in full color, the upper portions of several flowering stems which include a bud, a partially opened bud, and flowers in several stages of opening, the colors shown being as nearly true to those herein specified as is reasonably possible to obtain by conventional photographic procedures.

DESCRIPTION OF THE NEW PLANT

The following is a detailed description of our new carnation variety based upon observations of greenhouse grown plants at La Londe, Les Maures, France, the color designations being according to The R.H.S. Colour Chart published by The Royal Horticultural Society of London, England.

THE PLANT

Origin: Seedling.

Parentage:

*Seed parent.*—Stock Variety 78 OR 2.

*Pollen parent.*—Stock Variety 73 FOR 1. These parent varieties are individually identified in our collection of breeding plants and their origin and growth habits are recorded in our permanent records maintained in our office at 83250 La Londe, Les Maures, France.

Classification:

*Botanic.—Dianthus caryophyllus* hybrid.

*Commercial.*—Standard Carnation.

Form: A bush comprising at least four stems emitted from the main stem near the ground.

Height: About 90 cm. (in average) at eight months.

Main Stem:

*Length.*—Less than 15 cm. due to pinching.

Branching character: Few branches.

Growth habit: Vigorous, upright and very rigid.

Foliage:

*Quantity.*—Abundant.

*Number of leaves.*—More than 120.

*Leaf size, at the 7th Node.*—About 13.3 cm. long and about 1 cm. wide, in average.

*Leaf shape.*—Linear with acute apex and curved margins.

*Texture.*—Leathery.

*Color.*—Upper side — 189A. Under side — 189A.

*Leaflets.*—None.

*Ribs, veins and rachis.*—Hardly noticeable.

THE BUD

Size: Medium.

*Diameter.*—About 2 cm., in average.

*Length.*—About 3 cm., in average.

Shape: Ovoid.

Rate of opening: Normal for carnations.

Color of petals:

*When sepals first divide.*—4C, 4D and 50B, with 25D at the center of the petal.

*When petals begin to unfurl.*—4C and 50A, with 28D at the center of the petal.

Sepals:

*Number.*—Five.

*Shape.*—Joined at the lower part with the upper part generally ovoid and sharp pointed. The sepals are initially hooded over the bud and curl back when the flowers open.

*Color.*—Inside — 145C and 145B. Outside — 139C and 145B.

*Striae.*—The sepals are longitudinally striated.

Calyx:

*Shape.*—Funnel-shaped.
*Size.*—Medium large; medium in width and long.
*Splitting.*—The calyx does not split.
*Aspect.*—Smooth.

Flower stem:
*Length.*—About 68 cm., in average.
*Character.*—Erect and rigid.
*Color.*—189A.

THE FLOWER

Blooming habit: Recurrent and profusely during spring, midseason and fall with a tendency to give few blooms in fall.

Size: Medium.
*Diameter.*—About 7.8 cm., in average.
*Depth.*—About 5 cm., in average.

Borne; Singly.

Shape:
*When bloom first opens.*—Flat.
*When bloom matures.*—Flat.

Petalage:
*Number of petals.*—About 46, in average.
*Arrangement.*—Imbricated.
*Petal form.*—Fan-shaped with rounded edges and lightly ruffled margins.
*Texture.*—Leathery.
*Aspect.*—Satiny.
*Color.*—Outer Petal: Upper side, 4C with stripes of 50A at the outer margin and on the petal edges, with 28D at the center of the petal. Upper side base, greenish. Reverse side, 4C and 4D with longitudinal stripes of 50B and with 25D at the center of the petal. Inside Petal: Top side, 4C with 58A stripes at the outer margin and at the edge of the petal, and with 28D at the center of the petal. Base, greenish. Reverse side, 4C, 4D and 58B, with 25D at the center of the petal.

Petaloids:

*Number.*—Less than ten.
*Size.*—Smaller than the petals.
*Color.*—The same as the petals.

Flower stem:
*Length.*—About 68 cm., in average (cut at the tenth node).
*Character.*—Upright with good strength.
*Color.*—189A.

Discoloration after full bloom: Very slight.

Fragrance: Perceptible

Persistence: The flowers hang on and dry.

Lasting quality:
*As a cut flower.*—At least ten days in vase keeping.

REPRODUCTIVE ORGANS

Stamens:
*Number.*—10 to 14.
*Arrangement.*—Around the ovary.
*Anthers.*—Size: About 4 mm. Color: Lightly red.
*Filaments.*—Length: About 3.4 cm., in average. Color: Whitish.

Pistils:
*Number.*—Two.
*Styles.*—Length: About 2.6 cm., in average.
*Stigmas.*—Color: Lightly red.

Character of ovary: The ovary is ribbed.

This variety is very original and there are no other varieties of the same species which are in any way similar.

We claim:

1. The new and distinctive variety of carnation, substantially as herein shown and described, characterized by its intermittent flowering habit and profuse production of flowers having a generally fiery orange appearance; and the plant having a rapid and vigorous upright growth habit with medium long flower stems.

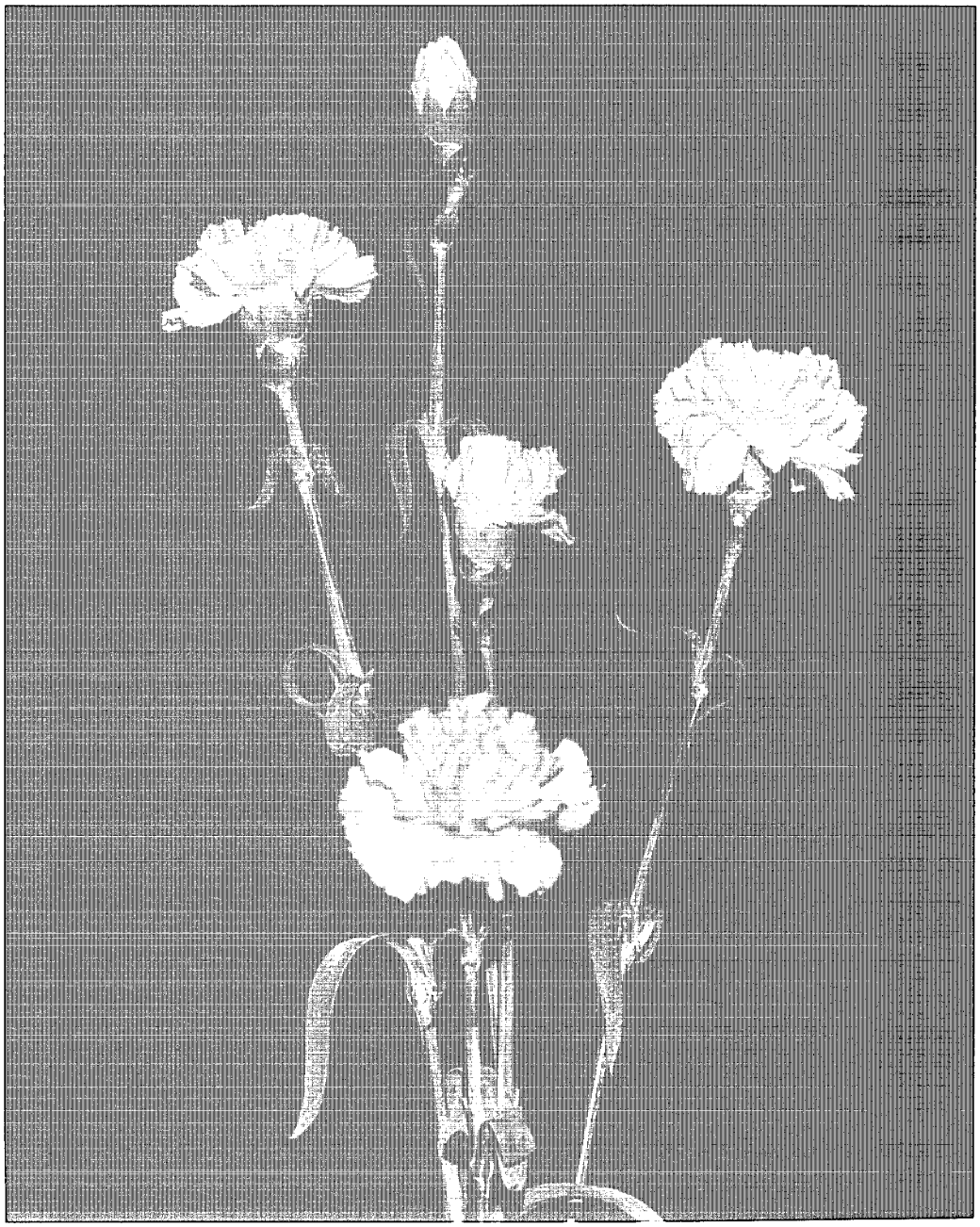

* * * * *